(12) United States Patent
Sudo et al.

(10) Patent No.: US 8,158,719 B2
(45) Date of Patent: Apr. 17, 2012

(54) BENZOXAZINE-FORMULATIONS WITH REDUCED OUTGASSING BEHAVIOUR

(75) Inventors: Atsushi Sudo, Tokyo (JP); Ryoichi Kudoh, Shiga (JP); Kazuya Uenishi, Nara (JP); Takeshi Endo, Yokohama (JP); Andreas Taden, Düsseldorf (DE); Rainer Schönfeld, Düsselsorf (DE); Thomas Huver, Düsselsorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 259 days.

(21) Appl. No.: 12/621,850

(22) Filed: Nov. 19, 2009

(65) Prior Publication Data

US 2010/0099818 A1    Apr. 22, 2010

Related U.S. Application Data

(63) Continuation of application No. PCT/EP2008/055939, filed on May 15, 2008.

(30) Foreign Application Priority Data

May 25, 2007    (EP) ..................................... 07010484

(51) Int. Cl.
*C08G 73/10*    (2006.01)

(52) U.S. Cl. ...................................................... 524/879
(58) Field of Classification Search ................... 524/879
See application file for complete search history.

(56) References Cited

U.S. PATENT DOCUMENTS

| 5,476,716 A | 12/1995 | Gallo |
| 5,910,521 A | 6/1999 | Johnson et al. |
| 6,376,080 B1 | 4/2002 | Gallo |

FOREIGN PATENT DOCUMENTS

| JP | 20072187 | 1/2007 |
| WO | WO03042196 | 5/2003 |
| WO | WO2008034814 | 3/2008 |

OTHER PUBLICATIONS

Kaushik, M. et al. "Thermal Behaviour of Benzoxazines—DGEBA Blends", International Journal of Plastics Technology, vol. 9, p. 377-384, 2005.

*Primary Examiner* — Edward Cain
(74) *Attorney, Agent, or Firm* — Steven C. Bauman

(57) ABSTRACT

Polymerizable combinations, comprising at least one first component selected from the group of benzoxazine monomers and at least one second component selected from the group of aromatic esters are described. Further on the use of aromatic esters as additives to benzoxazine monomers as well as methods of coating a device by heating the above mentioned combination, and a device, coated by that way is explained.

19 Claims, No Drawings

BENZOXAZINE-FORMULATIONS WITH REDUCED OUTGASSING BEHAVIOUR

This application is a continuation under 35 U.S.C. Sections 365(c) and 120 of International Application No. PCT/EP2007/055939, filed May 15, 2008 and published on Dec. 4, 2008 as WO 2008/145526, which claims priority from European Patent Application No. 07010484.9 filed May 25, 2007, which are incorporated herein by reference in their entirety.

The present invention is directed to a polymerizable combination, comprising at least one first component selected from the group of benzoxazine monomers and at least one second component selected from the group of aromatic esters, further on to the use of aromatic esters as additives to benzoxazine monomers as well as to a method of coating a device by heating the above mentioned combination, and also to a device, coated by that way.

Electronic devices such as circuit boards, semiconductors, transistors, and diodes are often coated with materials such as benzoxazine resins for protection. Such coating materials are often cured on the surface of an electronic device by heat.

The benzoxazine-containing molding compositions can be prepared by any conventional methods. For example, the ingredients (including resins and other additives) can be finely ground, dry blended, densified on a hot differential roll mill, and then followed by granulation. The molding composition, as described above, can be used for coating electronic devices such as semiconductors or circuit boards. The prepared compositions can be molded by any suitable molding apparatus. An example of such an apparatus is a transfer press equipped with a multi-cavity mold. For more detail on methods for preparing molding compositions and for coating electronic devices, see U.S. Pat. No. 5,476,716.

Benzoxazine is a heterocyclic compound that undergoes ring-opening polymerization. Based on this polymerization behavior, bi-, tri-, and multifunctional benzoxazine monomers undergo curing reaction.

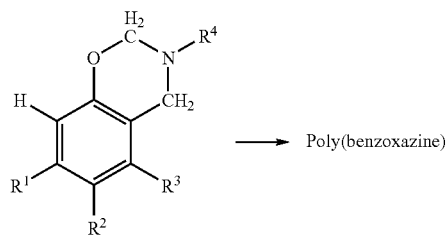
→ Poly(benzoxazine)

It is a highly relevant problem in practice, that there is significant out-gassing during the polymerization and curing reaction. Out-gassing occurs and may cause serious odor of amine.

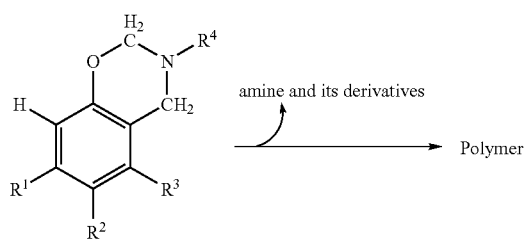
→ amine and its derivatives
→ Polymer

The out-gassing problem has also influence on various properties of cured materials which go hand in hand with a demand for high precision in size and preferably no bubble. For production of cured materials in a large scale, serious evolution of volatiles of amine derivatives have to be avoided to ensure the safety of operation environment.

Optimization of the manufacturing process alone to achieve a smooth outgassing during the curing reaction to make sure that no bubbles appear isn't successful.

Also the state of the art doesn't teach scavenger components, which sufficiently scavenge the amine and its derivatives involving imine in benzoxazine formulations.

E.g. isocyanate and isothiocyanate which are highly reactive with amine and imine, result in by-reactions with moisture, amine and $CO_2$ (or COS) gas.

If organic and inorganic acids are used to scavenge amine and imine, the formed salt dissociates into the original acid and amine (or imine) by heating. As polymerization/curing reaction of benzoxazine is carried out at elevated temperature higher than 100° C., the original amine is liberated at such conditions. Another issue is that the addition of such acids can decrease storage stability of the formulation. Further on the polymer must be thermally stable as much as possible for various applications of such polymers to structural materials, sealant and adhesives. Consequently it is a problem if outgassing is observed at higher temperatures later on.

Nevertheless it is known from the state of the art that epoxide is reactive with amine and thus can be expected to work as scavenger. E.g. Kaushik, M. et. al. have reported that addition of bisphenol A-diglycidyl ether to isothermal curing of benzoxazine reduced evolution of volatiles (International Journal of Plastics and Technology 2005, 9, 377-384). However, as will be revealed in the experimental part of the present invention, the addition of a usual epoxy containing component like bisphenol A-diglycidyl ether less than 10 mol % was only moderately effective to suppress weight loss during the isothermal curing reaction of benzoxazines. Besides the addition of epoxide leads to requirement for higher temperature for the curing reaction.

With other words the state of the art doesn't provide a proper solution for that problem presently.

Therefore the present invention was dedicated to make available a benzoxazine containing combination with low outgassing tendency during and after the polymerization.

Surprisingly this was achieved by a polymerizable combination, comprising at least one first component selected from the group of benzoxazine monomers and at least one second component selected from the group of aromatic esters. In a preferred embodiment the at least one benzoxazine monomer is selected from components according to formula 1:

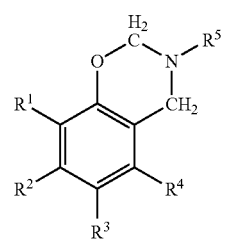
(I)

wherein
$R^1$=H;
$R^2$ is a linear or branched substituted or non substituted alkyl or aromatic group, preferably $R^{10}$ is a aromatic group;

$R^3$, $R^4$, $R^5$ are independently selected from hydrogen, linear or branched substituted or non substituted alkyl and aromatic group;
whereas $R^2$ and $R^3$ or $R^3$ and $R^4$ can optionally form a cyclic structure.

The at least one benzoxazine monomer according to formula I is preferably characterized by $R^2$, $R^3$, $R^4$, and $R^5$ comprising a further benzoxazine structure represented as

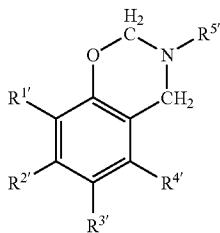
(II)

wherein $R^{1'}$, $R^{2'}$, $R^{3'}$, $R^{4'}$, and $R^{5'}$ are selected from hydrogen, linear or branched substituted or non substituted alkyl group and aromatic group.

In a preferred embodiment of the present invention the at least one benzoxazine monomer according to formula I is characterized by one of the formula

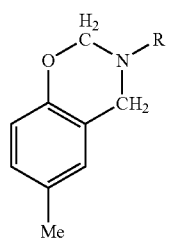
(III)

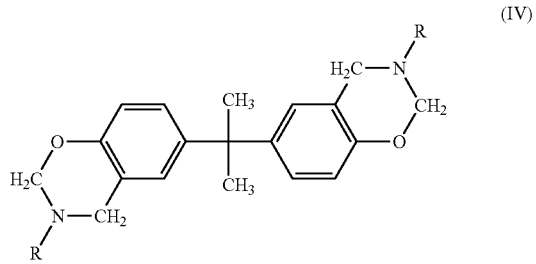
(IV)

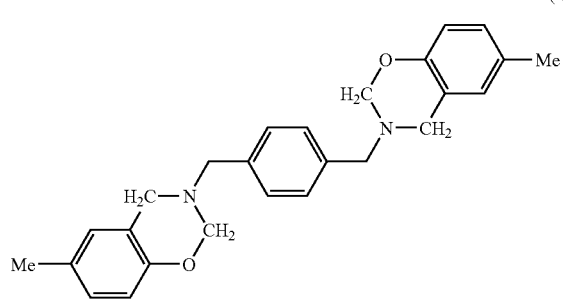
(V)

wherein R is a linear or branched substituted or non substituted alkyl or aromatic group and preferably R is selected from Methyl, Ethyl, 1-Propyl, 1-Butyl, Cyclohexyl, t-Butyl, Phenyl.

Without limiting the scope of the invention to those, there are listed below several examples for such monomers:

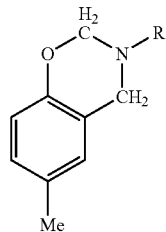

III-1: R = Mehyl
III-2: R = Ethyl
III-3: R = 1-Propyl
III-4: R = 1-Butyl
III-5: R = Cyclohexyl
III-6: R = tert-Butyl
III-7: R = Phenyl

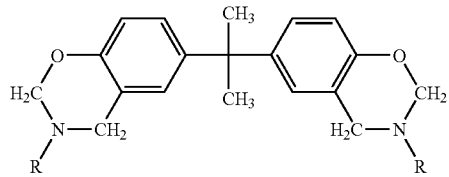

IV-1: R = Mehyl
IV-2: R = Ethyl
IV-3: R = 1-Propyl
IV-4: R = 1-Butyl
IV-5: R = Cyclohexyl
IV-6: R = tert-Butyl
IV-7: R = Phenyl A further preferred composition according to the present invention exhibits a molar ratio between said first and second component from 80:20 to 99:1 preferably from 90:10 to 98:2.

It is preferred that the composition according to the present invention comprises an aromatic ester selected from compounds according to formula VI:

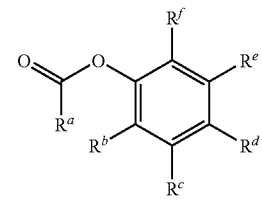
(VI)

wherein substituents $R^a$ to $R^f$ are independently same or different and denote hydrogen, a substituted or non substituted alkyl, aryl, alkaryl or aralkyl group having 1 to 20 carbon atoms, preferably $R^a$ and $R^b$ being connected to form a cyclic structure.

It is also preferred that at least one of the $R^c$, $R^d$, $R^e$, and $R^f$, denotes hydroxy group (—OH).

In a preferred embodiment of the present invention said aromatic ester component is selected from the group of lactones according to formula VIa:

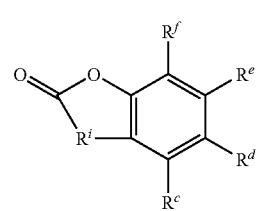
(VIa)

wherein $R^f$ is selected from any saturated or unsaturated alkyl bridge having linear or branched structure, wherein in particular the ring size of the lactone is 4 to 8 membered and especially preferred the ring size is 6-membered.

Thus it is highly preferred, that the ring size is 6-membered in particular as can be seen in formula (VIb) and (VIc).

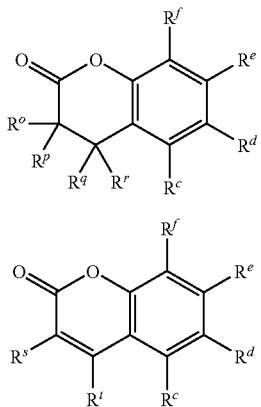

wherein R substituents are independently same or different and denote hydrogen;

a straight chain or branched alkyl group having 1 to 20 carbon atoms, preferably 1 to 12, most preferably 1 to 6 carbon atoms, like e.g. methyl, ethyl or propyl groups;

aryl, alkaryl or aralkyl groups, with preferably 6 to 20 carbon atoms, which can be directly bound to the aromatic or heteroaromatic moieties or 6-membered lactone moiety, or which can also be bound to those moieties by bridging atoms or bridging groups, like e.g. —O—, —S—, —(CO)—, —O—(CO)— or —(CO)—O—.

More preferably $R^o$, $R^p$, $R^q$, $R^r$, $R^s$, and $R^t$ denote for hydrogen or methyl group.

In a further preferred embodiment at least one of the $R^c$, $R^d$, $R^e$, and $R^f$, denotes hydroxy group (—OH). The presence of OH group on the aromatic ring enhances the reactivity of the aromatic ring with benzoxazine, or intermediate species in the polymerization/curing reaction, or polymer of benzoxazine.

It is also preferred that the composition according to the present invention comprises one or several further additives. Below there are mentioned several examples of additives for different purposes that can be included in the molding composition as well as the preferred ranges of their weight percent in the composition:

(1) A flame retardant such as a brominated epoxy novolac flame retardant (e.g., BREN, available from Nippon Kayaku). The preferred molding composition can contain up to 3.0 wt %, more preferably, 0.1-1.0 wt % of a flame retardant.

(2) A flame retardant synergist such as Sb 2 O 5 or WO 3. The preferred molding composition can contain up to 3.0 wt %, more preferably, 0.25-1.5 wt % of a flame retardant synergist.

(3) A filler such as silica, calcium silicate, and aluminum oxide. The preferred molding composition can contain 70-90 wt %, more preferably, 75-85 wt % of a filler.

(4) A colorant such as carbon black colorant. The preferred molding composition can contain 0.1-2.0 wt %, more preferably, 0.1-1.0 wt % of a colorant.

(5) A wax or a combination of waxes such as carnauba wax, paraffin wax, S-wax, and E-wax. The preferred molding composition can contain 0.1-2.0 wt %, more preferably, 0.3-1.5 wt % of a wax.

(6) Fumed silica such as aerosil. The preferred molding composition can contain 0.3-5.0 wt %, more preferably, 0.7-3.0 wt % of fumed silica.

(7) A coupling agent such as the silane type coupling agent. The preferred molding composition can contain 0.1-2.0 wt %, more preferably, 0.3-1.0 wt % of a coupling agent.

Further on it is preferred that the composition according to the present invention is curable at a temperature from 100° C. to 300° C., preferably from 150° C. to 250° C., more preferably from 130° C. to 160° C.

It is also preferred that the composition according to the present invention is curable at a pressure between 1 to 100 atm, most preferably under atmospheric pressure.

Further on a preferred composition according to the present invention comprises at least one further component selected from the group of catalysts, anorganic and/or inorganic fillers.

A further object of the present invention is a copolymerization and/or a polymerization product achievable by curing of a composition according to the present invention, preferably by usage of a range of curing temperature from 100° C. to 300° C., more preferably from 150° C. to 250° C., in particular from 160° C. to 200° C.

Also an object of the present invention is the use of an aromatic ester which is selected from compounds according to formula VI:

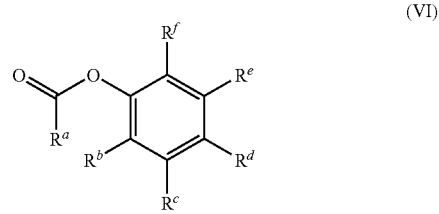

wherein substituents $R^a$ to $R^f$ are independently same or different and denote hydrogen, a substituted or non substituted alkyl, aryl, alkaryl or aralkyl group having 1 to 20 carbon atoms, preferably $R^a$ and $R^b$ being connected to form a cyclic structure as additive to benzoxazine monomers. In a preferred embodiment of the inventive use said additive contributes to a reduction of curing temperature and/or performs as gas scavenger to benzoxazine monomers. Therefore it is preferred, that said aromatic ester is suitable as scavenger, in particular for reducing the amount of out-gassing, especially for amines and its derivatives involving imine. Most preferably a said aromatic ester reduces the evolution of odor, which may come from amine or amine derivatives, during the curing reaction and/or reduces or even inhibits the appearance of bubbles.

In a further preferred use according to the present invention, in the aromatic ester according to formula VI at least one of the $R^c$, $R^d$, $R^e$, and $R^f$ denotes hydroxy group (—OH). For cases in which $R^a$ and $R^b$ aren't connected to form a cyclic structure it is preferred that they are hydrogen and/or any alkyl group (C1 to C20). Most preferably, $R^b$ should be hydrogen.

It is also a preferred use according to the present invention, that the aromatic ester component is selected from the group of lactones according to formula VIa:

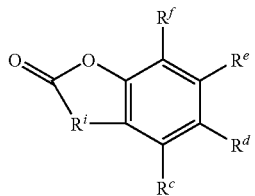

(VIa)

wherein $R^i$ is selected from any saturated or unsaturated alkyl bridge having linear or branched structure, whereas it is more preferred, that said aromatic ester component is selected from the group of lactones according to formula VIa, wherein the ring size of the lactone is 4 to 8 membered, in particular the ring size is 6-membered.

Thus it is highly preferred, that the ring size is 6-membered in particular as can be seen in formula (VIb) and (VIc).

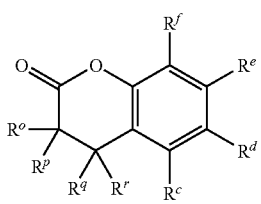

(VIb)

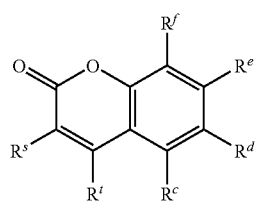

(VIc)

wherein R substituents are independently same or different and denote hydrogen;

a straight chain or branched alkyl group having 1 to 20 carbon atoms, preferably 1 to 12, most preferably 1 to 6 carbon atoms, like e.g. methyl, ethyl or propyl groups;

aryl, alkaryl or aralkyl groups, with preferably 6 to 20 carbon atoms, which can be directly bound to the aromatic or heteroaromatic moieties or 6-membered lactone moiety, or which can also be bound to those moieties by bridging atoms or bridging groups, like e.g. —O—, —S—, —(CO)—, —O—(CO)— or —(CO)—O—.

More preferably $R^o$, $R^p$, $R^q$, $R^r$, $R^s$, and $R^t$ denote for hydrogen or methyl group.

In a further preferred embodiment at least one of the $R^c$, $R^d$, $R^e$, and $R^f$, denotes hydroxy group (—OH). The presence of OH group on the aromatic ring enhances the reactivity of the aromatic ring with benzoxazine, or intermediate species in the polymerization/curing reaction, or polymer of benzoxazine.

It is also a preferred use according to the present invention, to have said benzoxazine component selected from components according to formula I:

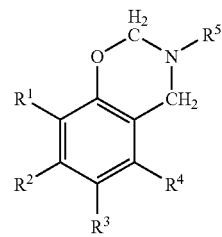

(I)

wherein $R^1$=H;

$R^2$ is a linear or branched substituted or non substituted alkyl or aromatic group, preferably $R^{10}$ is a aromatic group;

$R^3$, $R^4$, $R^5$ are independently selected from hydrogen, linear or branched substituted or non substituted alkyl and aromatic group;

whereas $R^2$ and $R^3$ or $R^3$ and $R^4$ can optionally form a cyclic structure.

Whereas it is also preferred that the above mentioned at least one benzoxazine monomer according to formula I is characterized by $R^2$, $R^3$, $R^4$, and $R^5$ comprising a further benzoxazine structure represented as

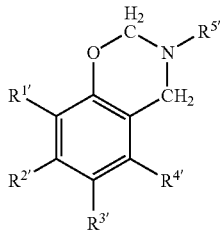

(II)

wherein $R^{1'}$, $R^{2'}$, $R^{3'}$, $R^{4'}$, and $R^{5'}$ are selected from hydrogen, linear or branched substituted or non substituted alkyl group and aromatic group.

In particular the at least one benzoxazine monomer according to the inventive use is characterized by one of the formula

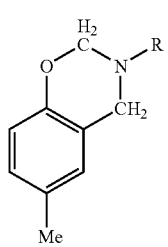

(III)

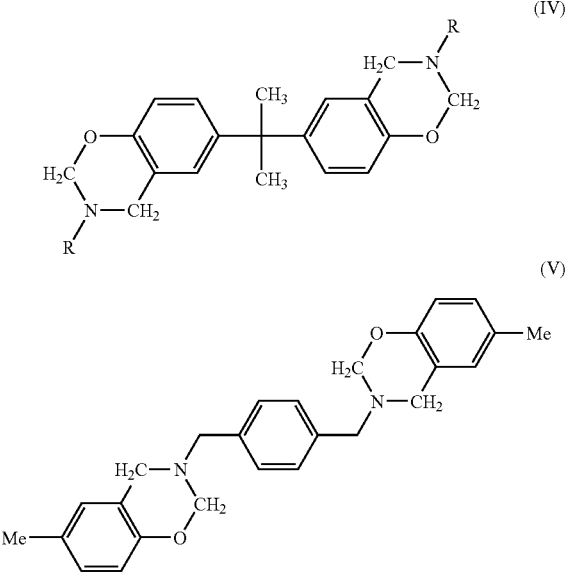

wherein R is a linear or branched substituted or non substituted alkyl or aromatic group and preferably R is selected from Methyl, Ethyl, 1-Propyl, 1-Butyl, Cyclohexyl, t-Butyl, Phenyl.

Without limiting the scope of the invention to those, there are listed below several examples for such monomers:

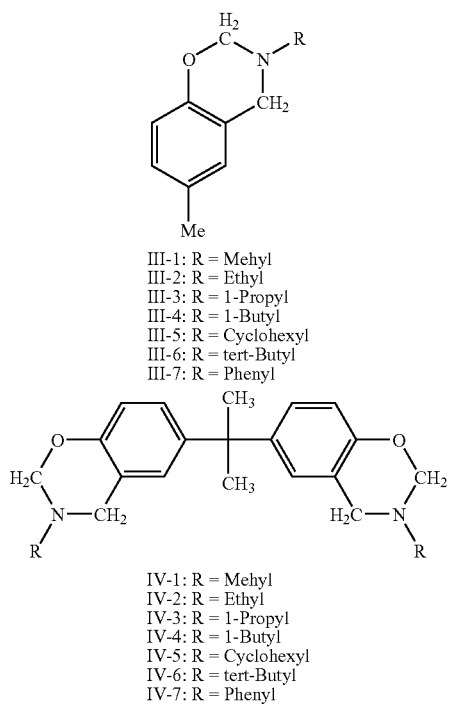

III-1: R = Mehyl
III-2: R = Ethyl
III-3: R = 1-Propyl
III-4: R = 1-Butyl
III-5: R = Cyclohexyl
III-6: R = tert-Butyl
III-7: R = Phenyl IV-1: R = Mehyl
IV-2: R = Ethyl
IV-3: R = 1-Propyl
IV-4: R = 1-Butyl
IV-5: R = Cyclohexyl
IV-6: R = tert-Butyl
IV-7: R = Phenyl In a further preferred use according to the present invention the molar ratio between said benzoxazine monomers and said lactone is 80:20 to 99:1 preferably 90:10 to 98:2.

The curable composition or a copolymerization and/or a polymerization product achievable from said composition according to the present invention are preferably used in the preparation of and/or as sealants, adhesives and/or coatings, preferably in electronic chip bonding and electronic chip underfills, whereby in particular the sealants, adhesives and/or coatings are applied to and hardened on or between substrates selected from the group comprising metals, silicates, metal oxides, concrete, wood, electronic chip material, semiconductor material and organic polymers.

Preferably the inventive use is directed to the application as adhesives where their low flammability is important (e.g. airplane interiors etc.) or where their thermal stability and easily modified physical properties such as modulus, tensile strength, and coefficient of expansion would be of value. As mentioned they could also be used in filled or unfilled molding applications, as matrix resins for fiber reinforced composite articles, as matrix resins for use in prepregs, or as matrix resins in advanced processes, such as resin transfer molding and resin film infusion.

Preferably the final compositions for the inventive use comprise additional components selected from the groups of inorganic fillers preferably silica powder, powdery metal oxide, and powdery metal or organic fillers preferably rubber particle and other polymer particles.

In a more preferred embodiment a composition and/or a copolymerization and/or a polymerization product according to the present invention is in the form of an adhesive, in which case one or more of an adhesion promoter, a flame retardant, a filler, a thermoplastic additive, a reactive or non-reactive diluent, and a thixotrope might be included. In addition, such an inventive adhesive may be placed in film form, in which case a support constructed from nylon, glass, carbon, polyester, polyalkylene, quartz, polybenzimidazole, polyetheretherketone, polyphenylene sulfide, poly p-phenylene benzobisoaxazole, silicon carbide, phenolformaldehyde, phthalate and napthenoate may be included.

The inventive compositions and/or copolymerization and/or polymerization products as well as pregregs and towpregs prepared therefrom are particularly useful in bonding of composite and metal parts, core and core-fill for sandwich structures and composite surfacing, and in the manufacture and assembly of composite parts for aerospace and industrial end uses, such as matrix resins for fiber reinforced composite articles, as matrix resins for use in prepregs, or as matrix resins in advanced processes, such as resin transfer molding and resin film infusion.

Another object of the present invention is a method of coating a device by heating a composition according to the present invention to a temperature sufficient to cure the composition, thus forming a polymer which coats a surface of the device, which preferably is an electronic device such as a semiconductor or a circuit board.

A further object of the present invention is directed to a device coated with a copolymerization and/or a polymerization product according to the present invention.

The present invention is exemplified in more detail by means of Examples, which follow below.

EXAMPLES

Example 1

To benzoxazine IV-1 (250 mg, 0.74 mmol), aromatic ester VIc (29 mg, 0.16 mmol) was added to obtain a homogeneous mixture. The mixture (5 mg) was isothermally cured (at 200° C. for 1 h) in thermo-gravimetric analyzer (TG) to monitor the corresponding weight loss during the curing reaction. TG analysis was carried out under nitrogen flow. The final weight loss was 0.1% (Table 1). 10 mg of the formulation was placed in a differential scanning calorimeter (DSC) and heated with a heating rate of 10 degree/min from 30° C. to 250° C. This analysis gave the corresponding profile of temperature-heat evolution relationship. The peak top in the profile was 166° C. (Table 2).

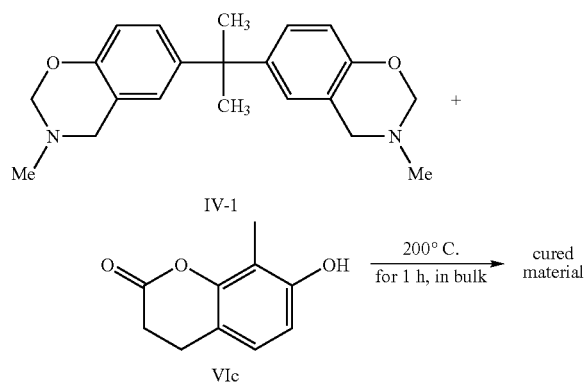

For comparison purposes the same experiment was performed without scavenger.

Referential 1:

No scavenger was used. IV-1 (5 mg) was isothermally cured (at 200° C. for 1 h) in thermo-gravimetric analyzer (TG) to monitor the corresponding weight loss during the curing reaction. TG analysis was carried out under nitrogen flow. The final weight loss was 1.2% (Table 1).

IV-1 (10 mg) was placed in a differential scanning calorimeter (DSC) and heated with a heating rate of 10 degree/min from 30° C. to 250° C. This analysis gave the corresponding profile of temperature-heat evolution relationship. The peak top in the profile was 191° C. (Table 2).

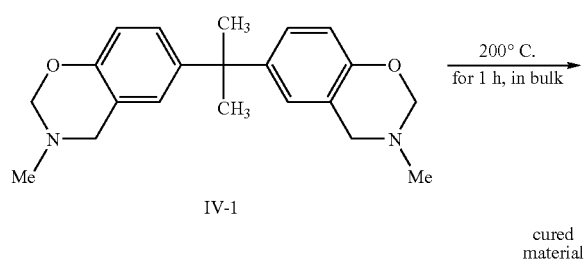

In another comparison test an epoxy based scavenger was used.

Referential 2:

Bis A-DGE was used as a scavenger. To benzoxazine IV-1 (250 g, 0.74 mmol), Bis A-DGE (28 mg, 0.082 mmol, epoxide moiety for trapping amine=0.16 mmol) was added to obtain a homogeneous mixture. The mixture (5 mg) was isothermally cured (at 200° C. for 1 h) in thermo-gravimetric analyzer (TG) to monitor the corresponding weight loss during the curing reaction. TG analysis was carried out under nitrogen flow. The final weight loss was 0.7% (Table 1).

10 mg of the formulation was placed in a differential scanning calorimeter (DSC) and heated with a heating rate of 10 degree/min from 30° C. to 250° C. This analysis gave the corresponding profile of temperature-heat evolution relationship. The peak top in the profile was 208° C. (Table 2).

TABLE 1

Weight loss upon isothermal curing reaction (monitored by TG)

| Example | benzoxazine | scavenger | weight ratio IV-1:scavenger | curing temperature | cured material weight loss/% |
|---|---|---|---|---|---|
| Ex 1 | IV-1 | VIc | 90:10 | 200° C. | 0.1 |
| Ref 1 | IV-1 | none | — | 200° C. | 1.2 |
| Ref 2 | IV-1 | Bis A-DGE | 90:10 | 200° C. | 0.7 |

TABLE 2

Peak top temperature for heat evolution (measured by DSC)

| Example | benzoxazine | scavenger | weight ratio IV-1:scavenger | peak top temperature |
|---|---|---|---|---|
| Ex 1 | IV-1 | VIc | 90:10 | 166° C. |
| Ref 1 | IV-1 | none | — | 191° C. |
| Ref 2 | IV-1 | Bis A-DGE | 90:10 | 208° C. |

Table 1 shows the high efficiency in suppression of weight loss by addition of the aromatic ester VIc. The conventional epoxy-type scavenger was only moderately effective.

Table 2 shows the addition effect of VIc on reducing temperature required for curing reaction. Addition of the conventional epoxy-type scavenger was disadvantageous.

The invention claimed is:

1. A polymerizable composition, comprising benzoxazine monomers and aromatic esters, wherein said aromatic esters are selected from compounds according to formula VI:

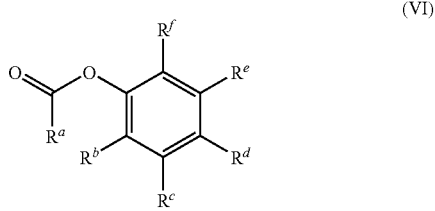

(VI)

wherein substituents $R^a$ to $R^f$ are independently the same or different and are selected from the group consisting of hydrogen, a substituted or non substituted alkyl, aryl, alkaryl or aralkyl group having 1 to 20 carbon atoms, or $R^a$ and $R^b$ are connected together to form a cyclic structure, and $R^c$ to $R^f$ are independently the same or different and are selected from the group consisting of hydrogen, a substituted or non substituted alkyl, aryl, alkaryl or aralkyl group having 1 to 20 carbon atoms.

2. A composition according to claim 1, wherein at least one benzoxazine monomer is selected from components according to formula I:

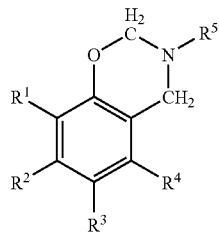

(I)

wherein

R¹=H;

R² is a linear or branched substituted or non substituted alkyl or aromatic group;

R³, R⁴, R⁵ are independently selected from hydrogen, linear or branched substituted or non substituted alkyl and aromatic group;

whereas R² and R³ or R³ and R⁴ can optionally form a cyclic structure.

3. A composition according to claim 2, wherein the at least one benzoxazine monomer according to formula I is characterized by R², R³, R⁴, and R⁵ comprising a further benzoxazine structure represented as

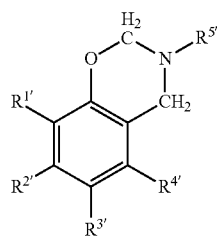

wherein R¹', R²', R³', R⁴', and R⁵' are selected from hydrogen, linear or branched substituted or non substituted alkyl group and aromatic group.

4. A composition according to claim 2, wherein the at least one benzoxazine monomer according to formula I is characterized by one of the formula

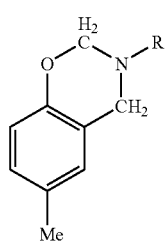

(III)

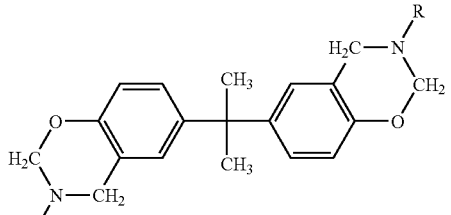

(IV)

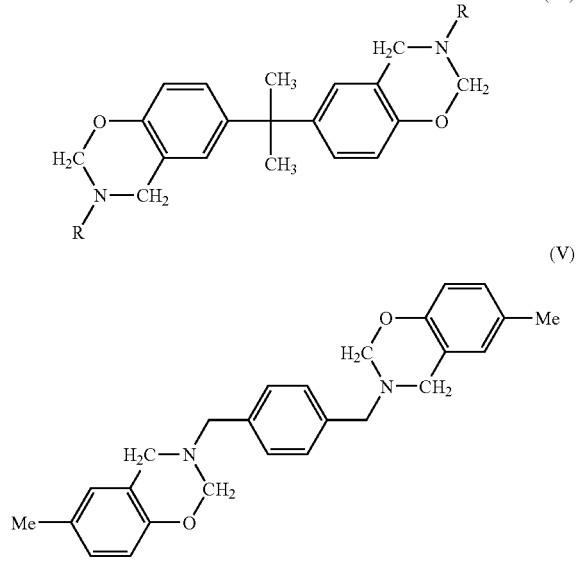

(V)

wherein R is a linear or branched substituted or non substituted alkyl or aromatic group.

5. A composition according to claim 1, wherein the molar ratio between said first and second component is 80:20 to 99:1.

6. A composition according to claim 1, wherein at least one of the Rᶜ, Rᵈ, Rᵉ, and Rᶠ, denotes hydroxy group (—OH).

7. A composition according to claim 1, wherein said aromatic ester component is selected from the group of lactones according to formula VIa:

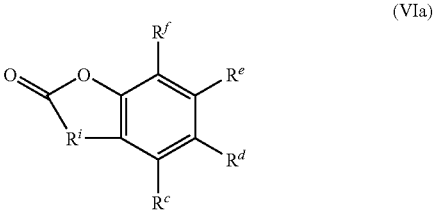

(VIa)

wherein Rⁱ is selected from any saturated or unsaturated alkyl bridge having linear or branched structure.

8. A composition according to claim 7, where said aromatic ester component is selected from the group of lactones according to formula VIa, wherein the ring size of the lactone is 4 to 8 membered, preferably the ring size is 6-membered.

9. A composition according to claim 1, wherein said composition is curable at a temperature from 100° C. to 300° C.

10. A composition according to claim 1, wherein said composition is curable at a pressure between 1 to 100 atm.

11. A composition according to claim 1, comprising at least one further component selected from the group of catalysts, anorganic and/or inorganic fillers.

12. A copolymerization and/or a polymerization product achieved by curing a composition according to claim 1.

13. A copolymerization and/or a polymerization product according to claim 12, produced by usage of a range of curing temperature from 100° C. to 300° C.

14. Method of coating a device by heating a composition according to claim 1 to a temperature sufficient to cure the composition, thus forming a polymer which coats a surface of the device.

15. Device coated with a copolymerization and/or a polymerization product according to claim 12.

16. Use of a composition according to claim 1 to coat a device by heating the composition to a temperature sufficient to cure the composition, thus forming a polymer which coats a surface of the device, wherein the aromatic ester component is selected from the group of lactones according to formula VIa:

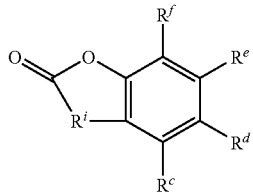

(VIa)

wherein $R^i$ is selected from any saturated or unsaturated alkyl bridge having linear or branched structure.

17. Use according to claim 16, wherein said aromatic ester component is selected from the group of lactones according to formula IIa, wherein the ring size of the lactone is 4 to 8 membered, preferably the ring size is 6-membered.

18. Use according to claim 16, wherein said benzoxazine component is selected from components according to formula I:

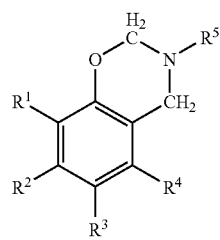

(I)

wherein
$R^1$=H;
$R^2$ is a linear or branched substituted or non substituted alkyl or aromatic group, preferably $R^{10}$ is a aromatic group;
$R^3$, $R^4$, $R^5$ are independently selected from hydrogen, linear or branched substituted or non substituted alkyl and aromatic group;
whereas $R^2$ and $R^3$ or $R^3$ and $R^4$ can optionally form a cyclic structure.

19. Use according to claim 18, wherein the at least one benzoxazine monomer according to formula I is characterized by $R^2$, $R^3$, $R^4$, and $R^5$ comprising a further benzoxazine structure represented as

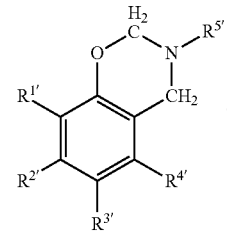

* * * * *